United States Patent
Kuusik et al.

(10) Patent No.: US 11,304,649 B2
(45) Date of Patent: Apr. 19, 2022

(54) SYSTEM AND METHOD FOR SELF-ASSESSMENT OF PHYSICAL CAPABILITIES AND CONDITION CHANGES

(71) Applicants: Tallinn University of Technology, Tallinn (EE); Motionmon OÜ, Tallinn (EE)

(72) Inventors: Alar Kuusik, Tallinn (EE); Katrin Gross-Paju, Tallinn (EE); Muhammad Mahtab Alam, Tallinn (EE)

(73) Assignees: Tallinn University of Technology, Tallinn (EE); Motionmon OÜ, Tallinn (EE)

(*) Notice: Subject to any disclaimer, the term of this patent is extended or adjusted under 35 U.S.C. 154(b) by 284 days.

(21) Appl. No.: 16/268,134

(22) Filed: Feb. 5, 2019

(65) Prior Publication Data
US 2020/0245920 A1 Aug. 6, 2020

(30) Foreign Application Priority Data

Feb. 5, 2018 (EE) .................. U201800003

(51) Int. Cl.
*A61B 5/00* (2006.01)
*A61B 5/22* (2006.01)
*A61B 5/11* (2006.01)

(52) U.S. Cl.
CPC .......... *A61B 5/4023* (2013.01); *A61B 5/0002* (2013.01); *A61B 5/0077* (2013.01);
(Continued)

(58) Field of Classification Search
CPC .......... A61B 5/1114; A61B 2562/0219; A61B 5/224; A61B 5/0002
See application file for complete search history.

(56) References Cited

U.S. PATENT DOCUMENTS

| 4,665,928 A | 5/1987 | Linial et al. |
| 5,485,402 A | 1/1996 | Smith et al. |

(Continued)

FOREIGN PATENT DOCUMENTS

| WO | 2012101093 A2 | 8/2012 |
| WO | 2013052586 A1 | 4/2013 |

(Continued)

OTHER PUBLICATIONS

Shin et al. "Within-day reliability of shoulder range of motion measurement with a smartphone" Feb. 16, 2012, Manual Therapy (Year: 2012).*

(Continued)

*Primary Examiner* — Eric F Winakur
*Assistant Examiner* — Jasim Ahmad Naeem
(74) *Attorney, Agent, or Firm* — Maine Cernota & Rardin (57) ABSTRACT

Disclosed is a system for objective self-assessment of physical capabilities and condition changes of individuals with conditions like multiple sclerosis, the system has a mobile device with an appropriate software for carrying out a set of tests for assessment of motor capabilities such as body balance, muscle strength, and muscle spasticity, and receiving assessment feedback. The system has inertial motion sensors for performing motion sensing, wherein said inertial motion sensors are integrated with said mobile device, e.g., a smartphone, a smart watch, or a personal computer, or in a separate wearable sensor device, connected with said mobile device over wired or wireless data connection. Also disclosed is a method for such self-assessment with such system.

11 Claims, 8 Drawing Sheets

(52) U.S. Cl.
CPC ........... *A61B 5/1114* (2013.01); *A61B 5/1116* (2013.01); *A61B 5/1122* (2013.01); *A61B 5/1125* (2013.01); *A61B 5/224* (2013.01); *A61B 5/681* (2013.01); *A61B 5/6898* (2013.01); *A61B 5/7405* (2013.01); *A61B 2562/0219* (2013.01)

(56) References Cited

U.S. PATENT DOCUMENTS

| | | | |
|---|---|---|---|
| 6,788,809 | B1 | 9/2004 | Grzeszcuk et al. |
| 7,141,026 | B2 | 11/2006 | Aminian et al. |
| 7,782,358 | B2 | 8/2010 | Nieminen et al. |
| 8,920,345 | B2 | 12/2014 | Greenberg et al. |
| 9,078,598 | B2 | 7/2015 | French et al. |
| 9,223,936 | B2 | 12/2015 | Aragones et al. |
| 9,301,712 | B2 | 4/2016 | McNames et al. |
| 9,451,916 | B2 | 9/2016 | Curtiss |
| 2011/0213278 | A1 | 9/2011 | Horak et al. |
| 2011/0224012 | A1 | 9/2011 | Hashimoto et al. |
| 2012/0310075 | A1 | 12/2012 | Russell |
| 2014/0163426 | A1 | 6/2014 | Alberts et al. |
| 2015/0133820 | A1* | 5/2015 | Zohar .................. A61B 5/1121 600/595 |
| 2015/0347717 | A1 | 12/2015 | Dalal et al. |
| 2016/0302710 | A1* | 10/2016 | Alberts .................. A61B 5/112 |
| 2017/0181689 | A1* | 6/2017 | Lin ...................... A61B 5/1122 |

FOREIGN PATENT DOCUMENTS

| | | |
|---|---|---|
| WO | 2014160451 A1 | 10/2014 |
| WO | 2018050746 A1 | 3/2018 |
| WO | 2018050763 A1 | 3/2018 |

OTHER PUBLICATIONS

Stieber et al. "Accurate Sample Time Reconstruction of Inertial FIFO Data", Dec. 13, 2017, Sensors (Year: 2017).*

Milosevic et al. "Wearable Inertial Sensor for Jump Performance Analysis", May 2015, Proceedings of the 2015 workshop on Wearable Systems and Applications (Year: 2015).*

Yeh et al. "Novel application of a Wii remote to measure spasticity with the pendulum test: Proof of concept", Jan. 2016, Gait Posture (Year: 2016).*

Rohleder et al., "Validation of Balance Assessment Measures of an Accelerometric Mobile Device Application Versus a Balance Platform", Wichita State University, May 2012 (Year: 2012).*

Plotz et al., "Automatic Synchronization of Wearable Sensors and Video-Cameras for Ground Truth Annotation—A Practical Approach", 2012 16th International Symposium on Wearable Computers, Jun. 2012 (Year: 2012).* https://www.power-systems.com/shop/category/jump-testers, Retrieved Mar. 13, 2019.

https://www.scienceforsport.com/vertec-jump-test/, Retrieved Mar. 13, 2019.

http://3dgaitanalysis.com/, Retrieved Mar. 13, 2019.

Gabel, Moshe, Ran Gilad-Bachrach, Erin Renshaw, and Assaf Schuster. "Full body gait analysis with Kinect." In Engineering in Medicine and Biology Society (EMBC), 2012 Annual International Conference of the IEEE, pp. 1964-1967. IEEE, 2012.

https://www.zephyranywhere.com/,. Retrieved Mar. 13, 2019.

Düking, Peter, Andreas Hotho, Hans-Christer Holmberg, Franz Konstantin Fuss, and Billy Sperlich. "Comparison of non-invasive individual monitoring of the training and health of athletes with commercially available wearable technologies." Frontiers in physiology 7 (2016).

Dobkin BH. Wearable motion sensors to continuously measure real-world physical activities. Current opinion in neurology. 2013;26(6):602-608. doi:10.1097/WCO.0000000000000026.

Porciuncula F., Roto A.V., Kumar D., Davis L, Roy S., Walsh C.J., Awad L.N., Wearable Movement Sensors for Rehabilitation: A Focused Review of Technological and Clinical Advances, PM R. Sep. 2018;10(9S2):S220-S232. doi:10.1016/j.pmrj.2018.06.013.

http://actigraphcorp.com/products-showcase/software/centrepoint-study-admin/, Retrieved Mar. 13, 2019.

http://www.actibelt.com/actibelt_flyer_march2010.pdf, Retrieved Mar. 13, 2019.

http://glneurotech.com/kinesia/applications/telemedicine/, Retrieved Mar. 13, 2019.

N. Mayerson and R. Milano, "Goniometric measurements in physical medicine," Archives of Physical Medicine and Rehabilitation, vol. 65, No. 2, pp. 92-94, 1984.

Kuusik, Alar; Gross-Paju, Katrin; Maamagi, Heigo; Reilent, Enar (2014) Comparative study of four instrumented mobility analysis tests on neurological disease patients, 2014 11th International Conference on Wearable and implantable Body Sensor Networks Workshops (proceedings); BSN2014 Jun. 16-19, 2014, Zurich, Switzerland; ISBN 978-0-7695-5178-4/14.

http://teaergo.com/wp/tea-behavior-analyses-products/captiv-motion/?lang=en, Retrieved Mar. 13, 2019.

Kuusik, A.; Kask, T.; Performance comparison of smartphones and a wearable motion sensor for patient m-assessment, in Proc Baltic Electronics Conference, Oct. 2018, DOI: 10.1109/BEC.2018.8600973.

Blast Golf stroke and swing analyzer, https://store.blastmotion.com/store/products/golf.

* cited by examiner

| Testing conditions: Sensor Recording Lite 3.10 software, Android OS | | | |
|---|---|---|---|
| Phone model | Target sampling period, ms | Actual average sampling period, ms | Standard deviation of sampling period, ms |
| Samsung Galaxy S7 | 10 | 11.4 | 0.52 |
| OnePlus 5 | 10 | 12.6 | 1.04 |
| OnePlus 6 | 10 | 14 | 0.88 |
| HUAWEI MYA-L11 | 10 | 12.6 | 1.95 |
| OnePlus A2003 | 10 | 14.5 | 1.00 |
| OnePlus 3T | 10 | 13.0 | 1.18 |
| Average | 10 | 13,01 | 1.095 |

FIG 7A

| Testing conditions: OnePlus A2003 smartphone, Sensor Recording Lite 3.10 software, Android 6.01 OS | | | |
|---|---|---|---|
| Target sampling period, ms | Actual average sampling period, ms | Standard deviation of sampling period, ms | Max recorded sampling period error, ms |
| 5 | 4.6 | 6.52 | 35 |
| 10 | 14 | 0.88 | 10 |
| 20 | 23.8 | 2.05 | 11 |

FIG 7B

| Device | Romberg | | Sharpened Romberg | | Tandem Romberg | |
|---|---|---|---|---|---|---|
| | EO | EC | EO | EC | EO | EC |
| Reference device | 13.1970 | 15.1551 | 14.3150 | 22.3311 | 15.9118 | 33.3214 |
| | 12.2367 | 11.0762 | 17.0255 | 16.0998 | 22.2713 | 28.8376 |
| | 12.7168 | 13.1156 | 13.8578 | 18.2658 | 16.5059 | 19.7289 |
| | 12.7168 | 13.1156 | 13.1660 | 19.3814 | 27.8241 | 19.9263 |
| Average | 12.7168 | 13.1156 | 14.5911 | 19.0195 | 20.6283 | 25.4536 |
| Samsung Galaxy S8 Edge | 13.2213 | 15.7524 | 15.3986 | 14.3297 | 33.0330 | 25.6973 |
| | 10.4655 | 13.3179 | 11.6248 | 14.9359 | 19.0499 | 30.0519 |
| | 15.5479 | 13.5722 | 17.3338 | 21.7824 | 11.4408 | 13.0048 |
| | 14.3878 | 13.3741 | 17.2337 | 19.6722 | 16.4522 | 28.1383 |
| Average | 13.4056 | 14.0042 | 15.3977 | 17.6800 | 19.9940 | 24.2231 |
| iPhone 6 | 10.7004 | 15.5028 | 12.0211 | 11.6705 | 17.5865 | 14.1711 |
| | 11.1644 | 11.7167 | 11.1626 | 13.3134 | 14.1949 | 13.5089 |
| | 11.4417 | 14.1321 | 11.2625 | 16.4237 | 14.6251 | 11.9652 |
| | 10.5957 | 12.1357 | 11.1076 | 15.5133 | 15.3603 | 12.6524 |
| Average | 10.9756 | 13.3718 | 11.3884 | 14.2302 | 15.4417 | 13.0744 |

FIG 8

| Device | Measured angle, deg | Noise level, deg/s |
|---|---|---|
| Reference wearable sensor | 90.5 | 0.1318 |
| Samsung Galaxy S8 Edge smartphone | 90.3 | 0.0976 |
| iPhone 6 smartphone | 90.7 | 0.0890 |
| Samsung Galaxy S8 Edge smartphone with Goniometer PRO app | 90.3 | --- |

FIG 9

SYSTEM AND METHOD FOR SELF-ASSESSMENT OF PHYSICAL CAPABILITIES AND CONDITION CHANGES

RELATED APPLICATIONS

This application claims priority from Estonian patent application No. U20180003, filed on Feb. 5, 2018, which is incorporated herein by reference in its entirety for all purposes.

BACKGROUND

Assessment of human physical capabilities is essential for athletes, elderly people, physically disabled persons, and patients with neuromuscular diseases. Assessment provides information about training progress or degradation of physical abilities related to living independence and safety. Assessment also provides information about relapse-remission episodes of progressive neuromuscular diseases and rehabilitation efficiency. Assessment can be done by visual observation, i.e. validating one's ability to stay, walk or jump; or with technological solutions providing quantified output, i.e. stop watches for measuring duration of Timed Up and Go (TUG) test, goniometers for joint motion range measurements, jump height testers, 3D camera systems for gait analysis that measure particular biomechanical parameters. 3D camera systems can be used for hand motion tracking and remote training support, in home environments as well. 3D camera systems have been used for assessment of changes of neurodegenerative disease patient condition. However, such method requires specific hardware setup and prepared testing area. Required resolution of linear displacement measurements for the assessment of human physical capabilities changes, i.e. during jumping test, is in a range of few millimeters ($\leq 5$ mm) that is difficult to achieve with consumer grade camera systems. Wearable motion sensors i.e. Zephyr Performance Systems are frequently used for athletes' physical capability assessment. Nike, Inc. is proposing to use wearable sensors and cameras for monitoring muscle fatigue progress during the training. However, it does not disclose any method for muscle fatigue progress monitoring and it does not cover other motor condition properties like balance deficit, presence of tremors, spasticity that are informative for elderly and physically weak persons. Motion sensors can be attached to sports equipment for evaluation of particular technical skills, i.e. golf swing. Wearable sensors, smart watches and smartphones can be used for classification of simple movements like walking, running, riding bicycle, resting. Counting amount of steps per minute and measuring duration and intensity of physical activity periods also represents physical abilities of the particular person and thus, the rehabilitation efficiency. Such wearable activity monitors are available by Actigraph (USA), Actibelt (Germany) and are dedicated for home use. However, such activity recorders cannot differentiate mobility deficits caused by physical condition changes or, i.e., by poor emotional states. Also, the required data collection time of activity recorders is at least one week making the system insensitive to rapid condition changes. Kinesia system (Great Lakes NeuroTechnologies, USA) has been developed for home based monitoring of Parkinson disease (PD) patients and counts bradykinesia, dyskinesia events. Kinesia solution is capable of sensing only PD specific motion patterns. Different tremors that are specific to PD can be differentiated using spectral density of motion signals. Wearable motion sensors are also used for single purpose assessment the risk of falls in older adults. There are available solutions targeting patient motion monitoring at hospital or ambulatory environments, i.e. by APDM (USA). APDM Mobility Lab solution relies on analyzing, and visualizing the movement data using a plurality of statistical signal processing methods particularly keeping in mind PD (ibid). Use of statistical methods is difficult in case of physically weak or disabled persons because the motion patterns are highly variable in time. Dedicated wearable motion sensors have sampling rate of at least 50 Hz that enables sufficiently accurate position calculations from linear acceleration sensor data (displacement error $\leq 5$ mm during normal speed human motions). Changes in human body condition are compared to a personal baseline or a group baseline. Therefore, the properties of particular motion sensor should not have an impact to the assessment results.

Figure 3:
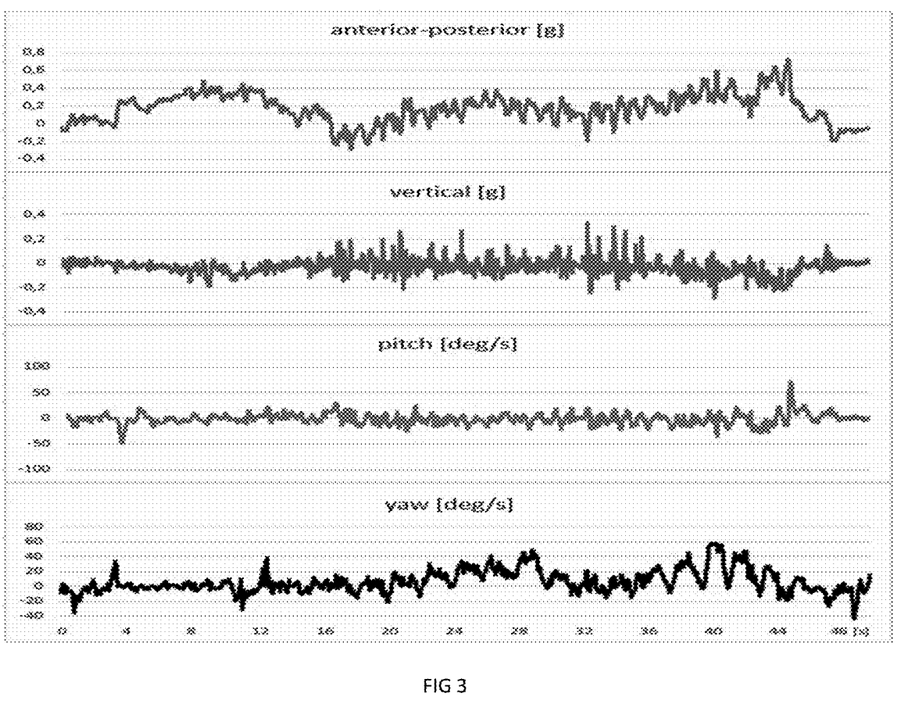
FIG. 3 is an example of an actual TUG recording of subject with moderate motor deficits.

For the assessment of physical abilities of weak people, i.e. elderly, certain tests are developed. Widely used tests include balance test (also named as postural sway test or Romberg test), range of motion (ROM) tests of extremities. Both linear and angular displacements are used in balance tests. Observed regions of balance tests are body center of mass and thorax. For repeatability purposes it is preferable to use angular displacement measures as far it does not depend on height of the subject and sensor placement height. For angular displacement measurements gyroscope sensor can be used. Known is instrumented balance testing method with a generic computer system. Known are postural sway measurements with handheld devices including three-component accelerometer; however, known solution does not give required precision and repeatability if a commercial smartphone is used as a handheld device. This is due to fact that proposed algorithm requires constant motion sensor sampling rate, which is not possible with existing non-real-time smartphone operating systems such as Android or iOS. Also, integration of linear acceleration as proposed in the invention will result in imprecise measurement results due to unstable sensor signal sampling rate. Range of motion (ROM) test of extremities in particular is used for characterizing conditions of muscles and joints. According to medical literature, the ROM measurement accuracy should be better than $\pm 5°$. Angular motion speed provides information about spasticity of muscles and can be used for rehabilitation efficiency assessment. Maximum range of motion as angle between body components is measured with a goniometer. However, its use requires assistance of trained medical personnel and it cannot be used for assessment of muscle dynamic characteristics. There are video-based range of motion measurement solutions available for extremities. Such solutions require camera setup and a special software. A computer-implemented method for ROM tests of different joints has been proposed. However, this known method does not propose technical implementations for applicable ROM measurements and does not address the impact of sampling rate deviations on the measurement results. Wearable range of motion (ROM) measuring instruments as electronic goniometers are proposed as well. There are also goniometric smartphone applications developed, for example Goniometer Pro. The application relies on gravity vector measurements and therefore can be used only for static measurement and does not provide information about angular motion speed. In context of wearable sensors use specific instrumented assessment tests are proposed. For example, APDM is proposing use of specific tests TUG, postural sway test, STEP test, PUSH test and their combination. In invention by Baker, Belachew et al. 2-Minute Walking Test (2MWT), 5 U-Turn Test (5UTT), postural sway test, and a set of cognitive test are proposed. According to research experiments, TUG and other complex motion signals of subjects with severe mobility deficits are computationally complex to analyze because of noises. Example of such recorded data is shown in FIG. 3. PUSH test requires assistance of physiotherapists or other skilled personnel. In postural sway test it is important to exclude pre-test and post-test motion artefacts. Usually assisting personnel is required for determining proper test start and end moments not applicable for unattended self-assessment. Tests proposed by APDM (ibid) and Baker (ibid) do not cover all relevant motor disorders, for example, muscle spasticity and strength. Muscle spasticity is traditionally examined with touching conducted by skilled physiotherapists. Monitoring of spectral content of electromuscular (EMG) signals and measuring muscle resonance frequencies with myometer device are known as well. Such methods require specific measurement instruments. There are also instrumented hand motion tests developed for touchscreen based cognitive skills assessment. However, assessment results of proposed methods may depend on properties of particular devices used, i.e. on used touchscreen size. Therefore, for the long-term human assessment clinically recognized tests and equipment, for instance 9-hole peg test (9-HPT) shall be used. Today there is no wearable motion sensor system known that is suitable for assessment of physical capabilities of weak, old or partially disabled subjects in home environments without the need for external assistance of skilled personnel. Known instrumented physical capabilities test sets are unsuitable for weak or disabled persons, lack of tests of muscle strength and spasticity measurements, or require human assistance to exclude off-test artefacts.

There exist solutions that wearable motion sensor data and video are monitored simultaneously. The same device has to be used for sensor data collection and video recording to maintain synchronization between the both signals. Alternatively, motion sensors and camera system have to be controlled with the same central coordinative device. In case of practical situations, especially for home use, it is difficult to use specific synchronization and camera devices. Therefore, means for synchronizing sensor data and video data from different sources, is further needed.

SUMMARY

The system comprises a mobile device, e.g., a smartphone, a smart watch or a tablet computer with appropriate software for carrying out a set of tests for assessment of motor capabilities and receiving assessment feedback. The set of tests comprises at least one test selected from a balance test or a postural sway test, a range of motion test of extremities, a jumping test, a spasticity test of extremities, 9-hole peg test and a self-assessment questionnaire with one to six numeric assessment results to each test. Motion sensing is performed by inertial motion sensors fixed to user's body. Preferably, the inertial motion sensors are inside the mobile device, i.e. inside the smartphone, a smart watch or a tablet computer. Alternatively, the inertial motion sensors may be inside a wearable sensor device or devices, connected to the mobile device over wired or wireless data connection.

The postural sway test is divided into eyes open and eyes closed test by an intensive motion marker in sensor signal intentionally produced by user performing agreed movement between eyes open and eyes closed testing phases. Preferably, the postural sway testing period is determined as a sum of defined time periods before and after motion marker in recorded into the sensor signal.

In one embodiment, the postural sway motion marker is artificially added to the motion signal by the mobile device during an audible signal indicating the end of eyes open testing phase and the beginning of the eyes close testing phase.

In one embodiment, spasticity is determined with measuring freed drop speed and range of lower extremities.

In one embodiment, the motion speed and trajectory error caused by the jitter of motion sensor sampling rate is compensated using timestamps of sampling events.

In one embodiment, the sensor data are synchronized with a video signal captured with an external video camera or cameras. For the synchronization, preferably, visible light signals are activated on movement monitoring device with simultaneous marking of sensor data stream with a specific signature. Video signal and sensor stream can be later synchronized with light signal and sensor signal signature.

Figure 7A:
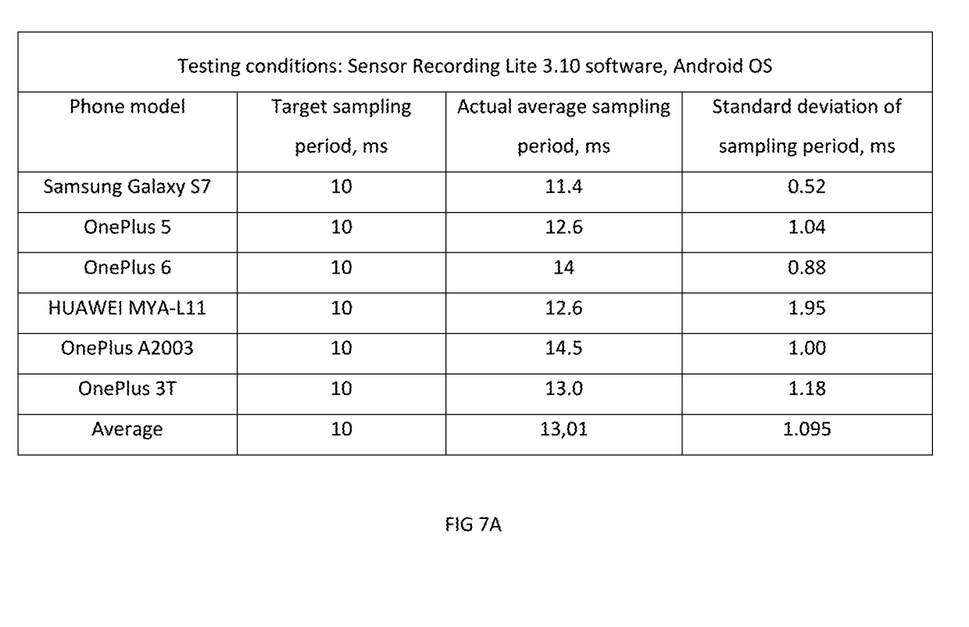
FIG. 7A shows variations of motion sensor sampling periods of six randomly selected Android smartphones
Figure 7B:
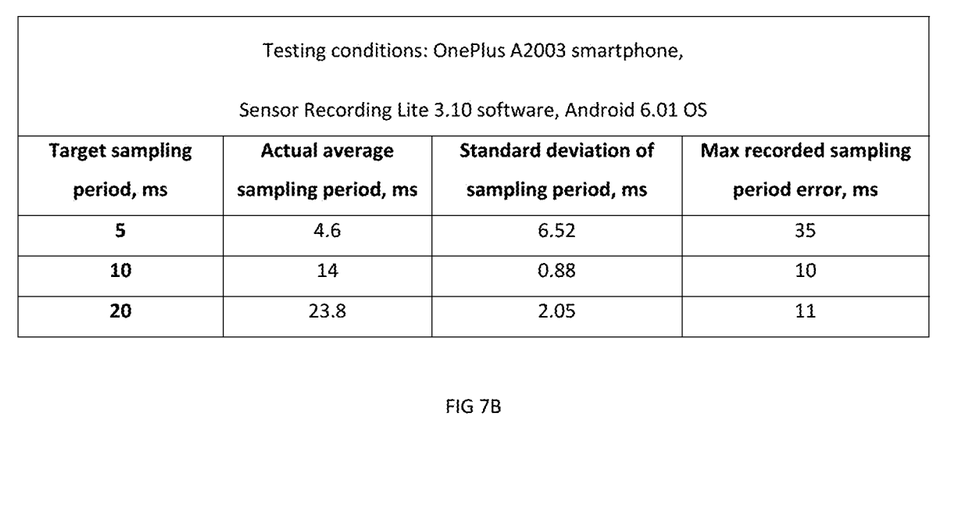
FIG. 7B shows variations between target sampling period and actual average sampling period of randomly selected Android smartphone (OnePlus A2003).

In one embodiment, the deviations of sensor sampling rate of mobile devices such as smartphones are taken into account by providing measuring results with time stamps. According to experiments, for sampling rates of 50 Hz and more, significant deviations in sampling period have been discovered as shown in FIG. 7.

DETAILED DESCRIPTION

A. Exemplary Remote Assessment System for Determining Physical Capabilities

Figure 1:
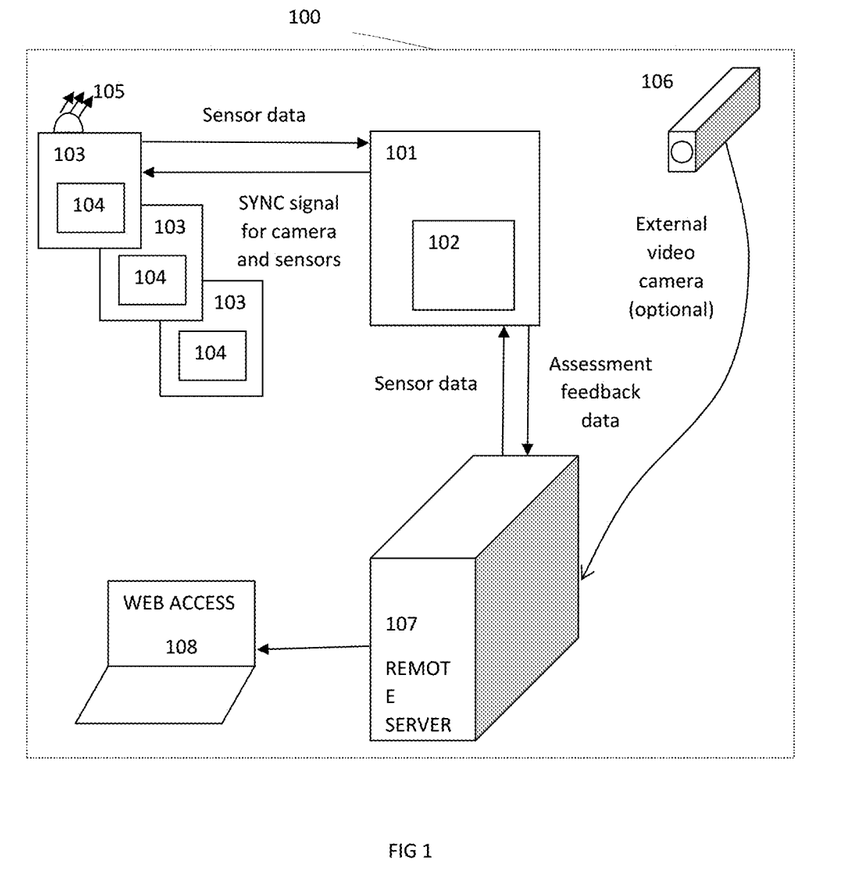
FIG. 1 is one embodiment of a system for personal assessment.

FIG. 1 illustrates one embodiment of a system for personal assessment which does not require assistive personnel in operation. The system 100 contains of a mobile device, e.g., a smartphone or smart watch or tablet computer 101. Mobile device 101 has an inertial motion sensing unit 102 comprising at least gyroscope sensor. One or more external wearable sensor 103 are connected to mobile device 101 over wireless link, for example Bluetooth Low Energy, SmartBan, WiFi or similar. Each wearable sensor 103 comprises a motion sensing unit 104. Motion sensing units 102 and 104 may also comprise at least a gyroscope but may also include an accelerometer, a magnetometer, a distance measurement sensor, an absolute position sensor like trilateration device. Output signals of motion sensor units 102 and 104 are combined with measurement timestamp or sample counter information for further correction of sampling jitter impact. Wearable sensors 103 have a light source 105, for example a light emitting diode (LED), wirelessly controllable from mobile device 101. LED light is detectible by external video camera 106. Simultaneously with activating LEDs 105 certain marker is written to output signals of motion sensors 104, enabling later offline synchronization of output signals of sensors 103 and recordings from camera 106. Mobile device securely transmits measurement results to a remote server 107, e.g., over an Internet. The remote server 107 preserves recorded data and performs sensor signal processing. Mobile device 101 may also perform sensor signal conditioning and local processing. During the processing numeric output of assessment test is calculated. The number of output parameters should be small, e.g., from one to six. Calculated numeric output parameters will be shown to test subject with appropriate user interface on mobile device 101. Individual and time series measurement results can be accessed through the conventional web interface on a computer 108. Camera 106 streaming data or recordings may also be sent to remote server 107 for simultaneous monitoring of sensor data and video.

B. Exemplary Self-Testing Procedure

Figure 2:
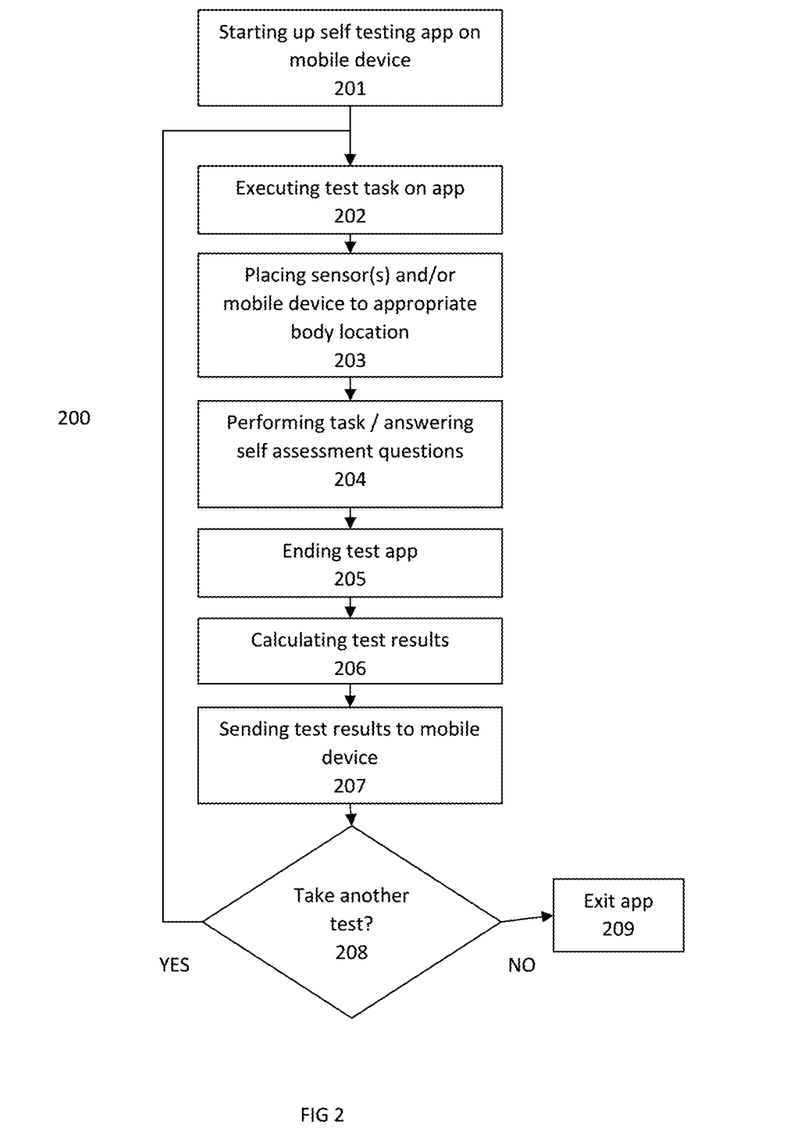
FIG. 2 is flow chart of an unassisted testing procedure according to one embodiment of the invention.

A flowchart of an unassisted testing procedure 200 according to one embodiment of the invention is shown on FIG. 2. Testing can be done at home environments without the need for any assistance. However, similar testing procedures could be used under supervised monitoring by coaches, physiotherapists and medical personnel. Test subject executes self-testing software application in step 201 on mobile device (such as 101 in FIG. 1) the subject selects particular test to me executed in step 202. Tests may include but are not limited to (a) balance test or postural sway test with eyes open and closed phases; (b) range of motion test of rising lower extremities; (c) spasticity test of relaxed lower extremities; (d) jumping test; (e) eyesight self-assessment test; (c) self-assessment test of body insensibility. With self-assessment tests user may add textual information that will be stored to remote server 107 together with measurement results. In step 203 user places wearable sensors 103 or mobile device 101 to dedicated body area as foreseen in testing procedure. In testing phase 204 user performs prescribed exercise(s) and/or answers self-assessment questions. After that user ends particular test in step 205 through the app. Collected data are automatically sent to the processing software in step 206. Processing can be done at a remote server (such as 107 in FIG. 1) or in the mobile device 101 or jointly by both devices. In step 206 calculated test results in a form of one to six numbers are sent to mobile device and presented to the user through the app. In step 208 user can select next test in step 202 or exit the testing application, step 209. As a unique property of the solution, none of testing tasks require assistance by another person.

C. Exemplary Individual Testing Exercises

With known solutions complex assessment tasks are used. For example, APDM is proposing using instrumented TUG test. However, TUG motion sensor signal of elderly and partially disabled people is noisy and difficult to process. An example of actual TUG recording of subject with moderate motor deficits is shown in FIG. 3. Therefore independent self-testing requires appropriate selection of testing exercises. The exercises should cover different parameter of human body including but not limited to body balance, muscle strength, and muscle spasticity.

A selection of appropriate physical capabilities tests suitable for self-assessment is presented. The selection is not final and other testing exercises may be added.

Performing postural sway test is as follows: user executes balance test in 202. User attaches mobile device 101, such as smart phone comprising sensor 102, or a special purpose device comprising a sensor 102, to a thorax with a stripe or holds tightly with one or preferably both hands. User stays still with eyes open for 10-20 seconds. User changes position, stretches body or performs other foreseen motion activity. User closes eyes and stays still with eyes closed for 10-20 seconds. User ends test in step 205.

Performing lower limb range of motion test is as follows: user executes ROM test in 202. In seated position user attaches mobile device 101 with sensor 102 as described above to a hip with a stripe or holds tight with a hand. User raises hip as quickly and as high as possible predefined amount of times, e.g., three to ten times. User ends test in step 205. User repeats the exercise with the second leg and terminates the test with step 205.

Performing spasticity test is as follows: user executes spasticity test in 202. In seated position user attaches mobile device 101 with sensor 102 as described above to a leg with a stripe. User raises a foot and lets it fall down freely. User ends test in step 205. User repeats the exercise with the second lower leg and terminates the test with step 205.

Performing jumping test is as follows: user executes jumping test in step 202. In standing position user attaches sensor 104 or mobile computer 101 to a hip with a stripe or holds tight with a hand. User jumps as high as possible predefined amount of times (3-10). User ends test in step 205.

C. Exemplary Description of Automated Processing of Acquired Data

Existing wearable assessment solutions of human motion capabilities and disorders require support of professionals in conducting testing procedures, extracting and interpreting results from the motion data. Therefore existing solutions are not suitable for independent and home-based human assessment. Also, several existing solutions are measuring certain mathematical features of motion like spectral power density, maximum acceleration, etc. that are hard to link with assessment metrics conventionally used by physiotherapists and coaches, such as whether the subject is able to stay, able to jump, maximum motion range of hip is 90 degrees, and require statistically valid amount of data. Current solution relies on direct feature extraction from sensor signal pattern, which allow automatic data processing and is insensitive to signal artefacts. Current solution automatically detects start and end of assessment exercises.

Figure 4A:
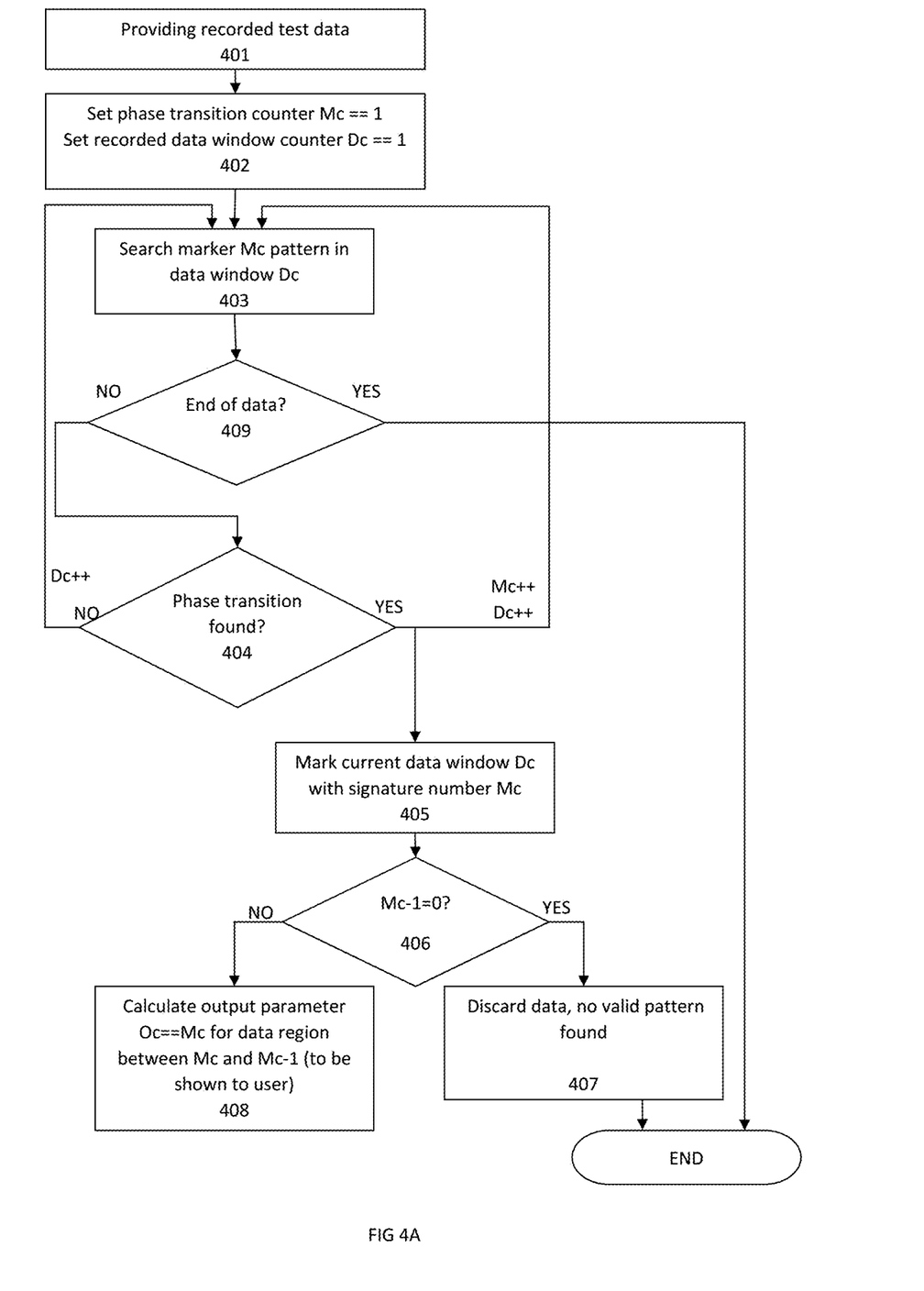
FIG. 4A is a flow chart of processing data of tests with multiple exercises, i.e. jumping test, ROM test and other similar tests.

Procedure of processing data of tests with multiple exercises, i.e. jumping test, ROM test and other similar ones is shown in FIG. 4A. At the beginning of testing signal processing procedure completed or streaming sensor data is provided 401. Data is analyzed in a sliding time window, wherein the data window size is one or more measurement samples. Data window counter Dc and specific motion phase transition marker Mc are set to "1" (Dc==1; Mc==1) in step 402. In the following phases specific motion signal transitions are searched for until the end of recording 408. The specific motion transition events might be and not limited only are zero accelerometer reading which means toe off the ground during jumping, zero angular speed which means maximum or minimum position of limb movements, high acceleration or angular velocity intentionally generated by the user. In case specific transition is found in data in step 403 particular time instance or time window is marked with particular phase transition counter in step 405. Output parameter, i.e. motion range, jump duration, motion speed is calculated from data marked with transition counter values Mc=n and Mc=(n−1), where n is a particular transition number. Output parameters are counted as Oc==Mc and may be presented to user as an individual assessment results, could be combined or averaged. If at least two phase transition markers are not found (Mc<2) in recorded signal of repeated exercises, then data is discarded as no valid one in step 407.

Figure 4B:
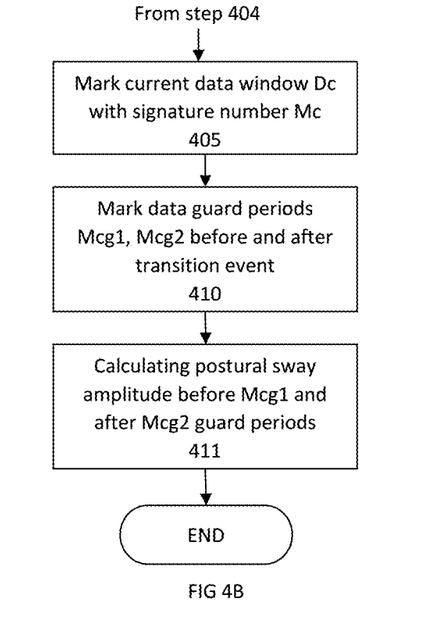
FIG. 4B is a flow chart of processing of postural sway signal and other non-repeatable tests with a single phase transition marker.
Figure 5:
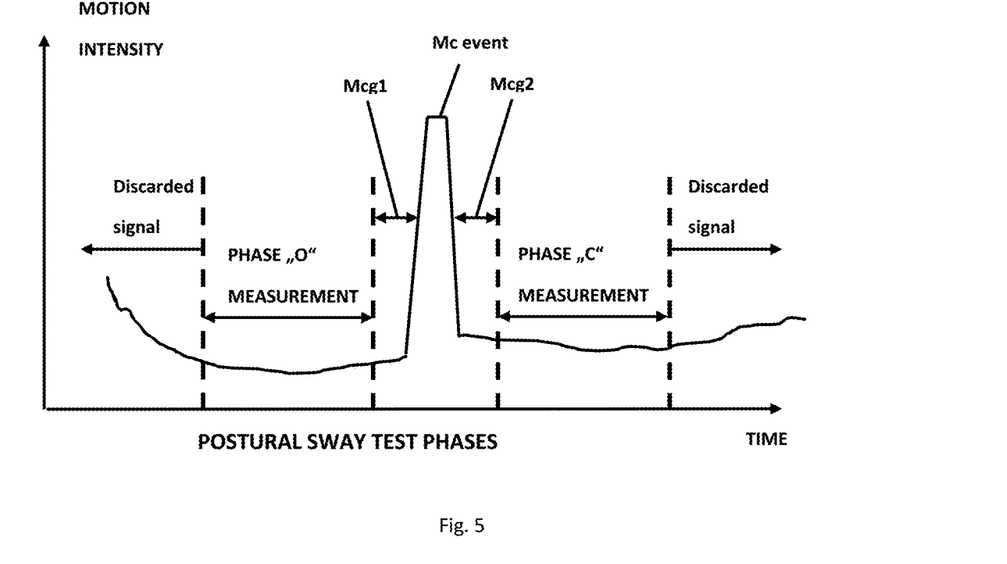
FIG. 5 illustrates postural sway phase separation according to one embodiment of the invention.

Processing of postural sway signal and other non-repeatable tests with a single phase transition marker is different as shown in FIG. 4B. In postural sway test phases with eyes open (phase O) and close (phase C) have to be separated. It is preferred that user makes both tests without significant changes in body position because such changes directly affect the testing outcomes. Giving certain audiovisual or haptic request for transition phase O->C is not recommended, because user may be late starting phase C resulting imprecise testing outcomes as well. In current solution embodiment user generates specific motion pattern between phase O and C, which could be a turning, shaking or other similar intensive motion that is registered with the motion sensors 102 or 104. Alternatively artificial intense motion marker can be inserted to motion recording during an audible signal by sensor device that indicates eyes open phase end and the beginning of the eyes close phase to user. After the phase transition detection, guard time moments Mcg1 and Mcg2 before and after phase transition event Mc are set to sensor data in step 410. Guard time duration of 1 second before and after phase transition is sufficient according to the testing results. Postural sway measure as a maximum displacement of upper body, average swing or any other similar parameter is calculated in step 411. Typically 10 seconds of stable standing is required for both testing phases (O, C), therefore the duration of total data recording should be 20-30 seconds. FIG. 5 illustrates postural sway phase separation method.

Figure 9:
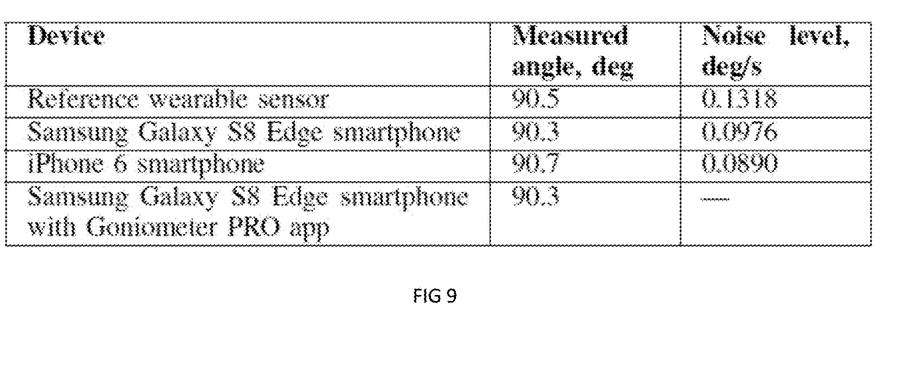
FIG. 9 is a comparative study of 90° slow motion accuracy test run on two smartphones (Samsung S8, iPhone 6) and a reference device.

D. Exemplary Method for Reducing Measurement Errors Caused by Sampling Period Jitter Devices operating with non real time software and operating systems suffer time deviations in task executing. Smartphones belong to such device category. Due to deviation of sampling period of motion sensor 102 the smartphones in function of mobile computer 101 cannot provide accurate angular measurements for the postural sway or ROM if the sampling period variations are not taken into the account. Variations of motion sensor sampling periods of six randomly selected Android smartphones are presented in FIG. 7. The target sampling period was set to 10 ms, Sensor Recording Lite 3.10 software was used in experiment. Actual average sampling period was measured. In second experiment, an average gyroscope sampling period was used to calculate rotation angle of two Android smartphones (see FIG. 9). 90 degree rotation calculated from gyroscope data assuming constant sampling rate gave errors of 2.5° (Google Nexus 5) and 6.3° (Samsung Galaxy 7S) respectively. Measurements performed with different mobile computers and software setups without measurement period adjustments are not comparable. Current embodiment calculates motion angle Θ (in degrees) by formula $$\Theta = \omega * (T_k - T_{k-1}) \qquad (1)$$

between two sensor samples, where ω is angular velocity (degrees/s) and $T_k$ and $T_{k-1}$ are timestamps (s) of k-th and its previous angular velocity measurement moment respectively.

Whole range of motion of n measurements is calculated as $$\Sigma_{k=1}^{n} \omega_k (T_k - T_{k-1}) \qquad (2)$$

According to tests with two phones gyroscopic angular measurement error was 0.3° (iPhone 6, iOS) and 0.7° (Samsung Galaxy S8, Android) after 90 degrees of rotation using timestamps based rotation angle calculations.

E. Testing Results with Disclosed Embodiments

Figure 6A:
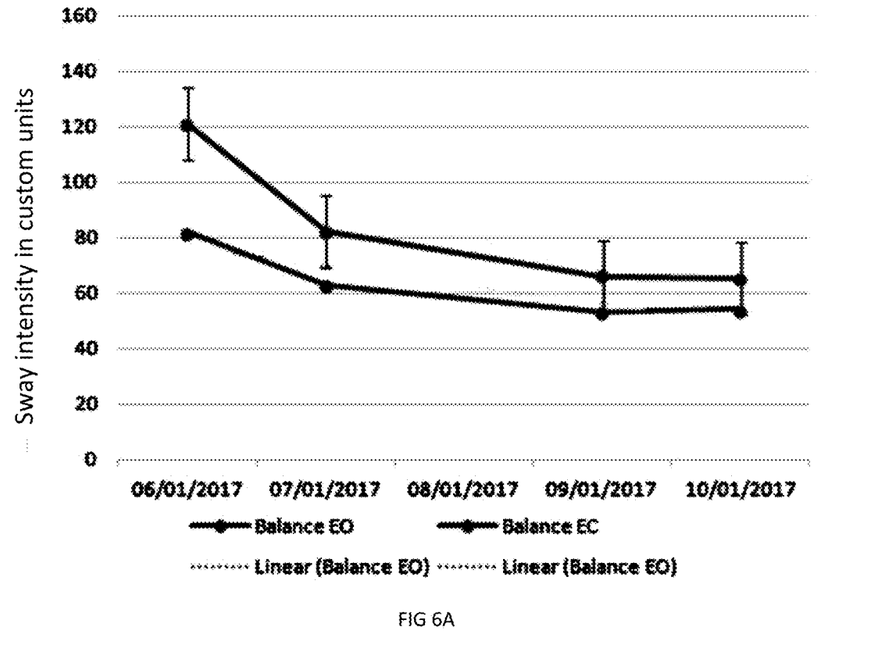
FIGS. 6A and 6B show sensitivity data of proposed solutions for body stability and lower limb ROM respectively.
Figure 6B:
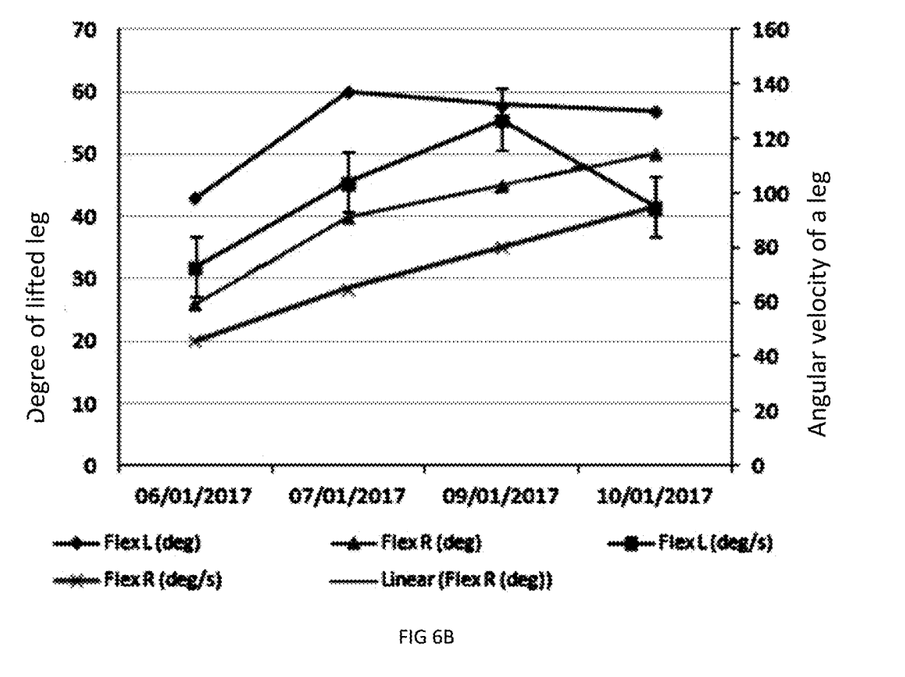

FIG. 6A and FIG. 6B represent sensitivity of proposed solution for different body functions (body stability and lower limb ROM) affected with intensive therapy. Vertical bars presents 2STDEV range FIG. 6A and FIG. 6B demonstrates that the proposed system is sensitive to daily changes in motor capabilities. Graphs present improvement of motor capabilities of a subject during the therapy. Postural sway is decreasing, characterizing improvements in balance; range and speed of movement of lower limbs is increasing, characterizing improvements in muscle strength. Improvements were confirmed with traditional assessment methods by a trained physiotherapist.

Figure 8:
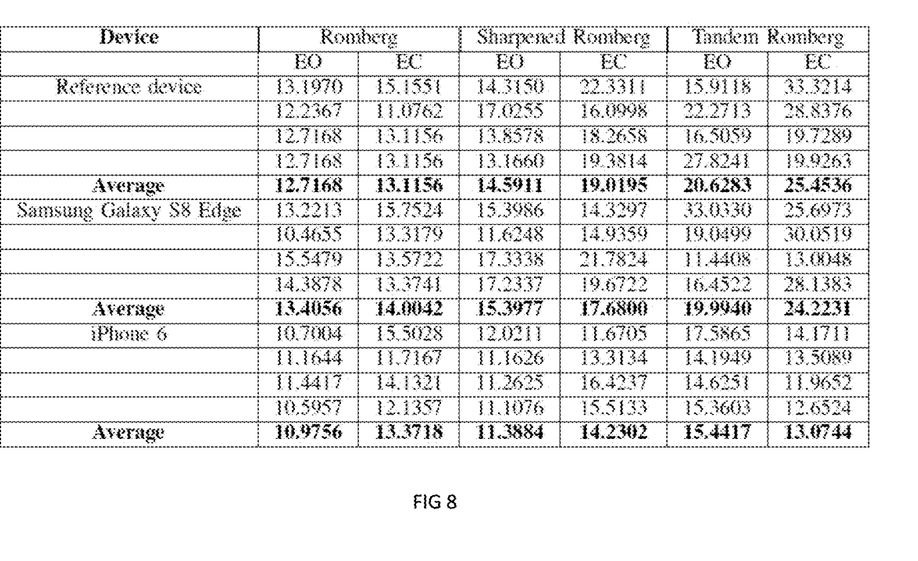
FIG. 8 is a comparative study of Romberg test, Sharpened Romberg test and Tandem Romberg test run on two smartphones (Samsung S8, iPhone 6) and on reference device. A healthy volunteer of 13.5 years old was requested to perform three different Romberg tests with smartphones and reference wearable device. Measuring device was attached to the middle of thorax. All devices were configured to 50 Hz of sampling rate, actual durations of sampling periods of smartphone sensors were determined through the measurement timestamps. A numeric balance characterizing parameter was calculated from angular velocity of gyroscopes all three devices. Table on FIG. 8 characterizes deviations of measurement results in experiments.

The results and their average for variant Romberg balance tests with both smartphones and the reference motion sensor are shown on FIG. 8. In conducted tests two different smartphone models were used: Samsung Galaxy S8 Edge with 6-degrees of freedom (6-DOF) 16-bit IMU LSM6DSL (STMicro) IMU and iPhone 6 with 6-DOF 16-bit (expected resolution, public data not available) IMU MP67B (TDK/Invensense). Only gyroscope sensor data was used for conducted motion measurements. Both sensors were configured to 1000 dps of full scale of angular velocity, data sampling rate was set to 50 Hz. Sensor data was recorded with Sensor Recording 2.22 PRO (Android) and Physics Toolbox Sensor Suite (iOS) software applications. Both software applications provide timestamps of actual measurements taken. For the Samsung Galaxy S8 Edge device the real motion sensor sampling rate was 45.31 Hz with STDEV with STDEV 0.231 Hz. Reference data was acquired with a wearable motion sensor having 9-DOF 16-bit BN0055 IMU (Bosch Sensortec). Reference sensor had IMU sampling rate of 50.78 Hz with STDEV 0.099 Hz. 0.309 Hz. iPhone 6 had actual sampling rate of 50.10 Hz The difference increased exponentially within growing Romberg test difficulty (Tandem Romberg being the most difficult to execute). Statistical analysis using two-sample t-Test while assuming equal variance within 95% CI (confidence intervals) showed no statistical difference between the reference device and the smartphones (t Stat<t Critical two-tail and P 0:05 in order to reject H0), 2:2281 6<0:2352 for Samsung Galaxy S8 Edge (P-value 0:8188) and 2:2281 6<2:0853 for iPhone 6 (P-value 0:0636) respectively. Taking also into consideration the angular speed noise levels of each sensor device, uncertainty of measurement in the analysis of this article still is within the accepted reference range for medical measurements (5 degrees) (0:7908, 0:5856, 0:534 respectively).

What is claimed is:

1. A system for objective self-assessment of physical capabilities of a person, said system comprising:
a mobile device, a software executed on said mobile device for carrying out a set of self assessment tests for assessment of motor capabilities, said tests selected from a group comprising body balance, muscle strength, muscle spasticity, and hand dexterity, and for receiving assessment feedback;
at least one inertial motion sensor for performing motion sensing, wherein said inertial motion sensor is integrated with said mobile device, selected from a group consisting of a smartphone, a smart watch, a personal computer, or in a separate wearable sensor device, wherein said inertial motion sensor is connected with said mobile device over a wired or a wireless data connection, wherein said set of tests comprises a postural sawy test, wherein said software is configured to divide said postural sway test into an eyes open phase and an eyes closed phase separated by either a motion marker in the sensor signal intentionally produced by the user performing an agreed sudden movement or by an artificially generated motion marker in the sensor signal produced by said mobile device during an audible signal indicating a transition between said eyes open phase and said eyes closed phase.

2. The system of claim 1, wherein said set of self-assessment tests further comprises a range of motion test of extremities providing motion range and speed data.

3. The system of claim 2, wherein an angular motion range is calculated based on said mobile device gyroscope angular velocity readings and motion speed and trajectory error caused by the jitter of motion sensor sampling rate is compensated using timestamps of sampling events.

4. The system of claim 1, wherein said set of self-assessment tests further comprises a jumping test providing information about jumping time or height, a spasticity test of extremities, or a 9-hole peg test with one to six numeric assessment results to each test.

5. The system of claim 4, wherein linear accelerometer measurement error caused by the jitter of motion sensor sampling rate is compensated using timestamps of sampling events.

6. The system as in claim 1, wherein said software is configured to segment said motion sensor signals into measurement phases based on specific shape markers in the motion signal, and to disregard recorded data far before and after the markers is discarded as noise before and after the testing procedure.

7. The system of claim 1, wherein said spasticity is determined with measuring free drop speed and range of motion of lower extremities of the patient.

8. A system for objective self-assessment of physical capabilities of a person, said system comprising:
a mobile device,
a software executed on said mobile device for carrying out a set of self-assessment tests for assessment of motor capabilities, said tests selected from a group comprising body balance, muscle strength, muscle spasticity, and hand dexterity, and for receiving assessment feedback;
at least one inertial motion sensor for performing motion sensing, wherein said inertial motion sensor is integrated with said mobile device, selected from a group consisting of a smartphone, a smart watch, a personal computer, or in a separate wearable sensor device, wherein said inertial motion sensor is connected with said mobile device over a wired or wireless data connection, wherein said system comprises at least one video camera for recording said tests, said mobile device is equipped with a light indicator and said software is configured to activate said light indicator and synchronize said video signal captured by said at least one video camera with light signals from said mobile device, with simultaneously marking of said sensor data stream with a specific signature.

9. A method for self-assessment of physical capabilities and changes in a physical condition of a person, in a system, the method comprising:
providing an inertial motion sensor tightly attached to the person's body for measuring a body movement;
carrying out at least one test of self assessment of motor capabilities, said test selected from a group consisting of a body balance, a muscle strength, a muscle spasticity and a hand dexterity and collecting data;
sending collected data to a processing software executed in a mobile device or a remote server;
determining the change in said physical condition if at least one of the following measured parameters have changed between two consecutive measurements as follows: balance is worsening if postural sway amplitude has increased; muscle strength is decreasing if range of motion test motion amplitude has decreased or range of motion test speed has decreased or jumping height has decreased; spasticity is increasing if spasticity test motion range is decreased; and parameters are improved if opposite changes have occurred, and
video recording of the performed test and wherein said software is configured to synchronize said video recording and said signal from motion sensor by activating a light indicator on the motion sensor, and simultaneously adding a specific signature at said signal from motion sensor.

10. Method as in claim 9, comprising the steps of execution of balance test, range of motion test of extremities, jumping test, spasticity test of extremities and providing one to six numeric assessment results after each test.

11. Method as in claim 10, wherein in said range of motion test of extremities, said software is configured to calculate motion range based on angular speed and timestamps provided by said motion sensor.

* * * * *